United States Patent

Wu et al.

[11] Patent Number: 5,591,689
[45] Date of Patent: Jan. 7, 1997

[54] PREPARATION OF ISOMERIZATION CATALYST COMPOSITION

[75] Inventors: An-hsiang Wu, Bartlesville; Charles A. Drake, Nowata; Ralph J. Melton, Bartlesville, all of Okla.

[73] Assignee: Phillips Petroleum Company, Bartlesville, Okla.

[21] Appl. No.: 494,832

[22] Filed: Jun. 23, 1995

[51] Int. Cl.$^6$ .................................................. B01J 23/42
[52] U.S. Cl. .................... 502/334; 585/741; 585/482; 502/326; 502/327; 502/333; 502/335
[58] Field of Search ................................. 502/229, 230, 502/231, 326, 327, 333, 334, 335

[56] References Cited

U.S. PATENT DOCUMENTS

| | | | |
|---|---|---|---|
| 2,900,425 | 8/1959 | Bloch et al. | 260/666 |
| 3,112,351 | 11/1963 | Hoekstra et al. | 260/683.75 |
| 3,231,517 | 1/1966 | Bloch et al. | 252/442 |
| 3,248,320 | 4/1966 | White et al. | 208/136 |
| 3,903,195 | 9/1975 | Franck et al. | 260/683.68 |
| 3,923,915 | 12/1975 | Franck et al. | 260/666 P |
| 3,993,594 | 11/1976 | Myers et al. | 252/442 |
| 4,014,948 | 3/1977 | Myers et al. | 260/666 |
| 4,149,993 | 4/1979 | Rao et al. | 252/442 |
| 4,283,585 | 8/1981 | Legendre et al. | 585/482 |
| 4,480,048 | 10/1984 | Bournonville et al. | 502/227 |
| 5,004,859 | 4/1991 | Schmidt et al. | 585/741 |

*Primary Examiner*—Glenn A. Galdarola
*Assistant Examiner*—Nadine Preisch
*Attorney, Agent, or Firm*—Charles W. Stewart

[57] ABSTRACT

A Group VIII metal and chloride-containing composition (effective as an alkane/cycloalkane isomerization catalyst) is prepared by a method which comprises mixing aluminum trichloride with a solid material containing at least one Group VIII metal (Pt and/or Pd and/or Ni) and alumina, heating the obtained mixture in an inert gas at about 450°–750° C., and then treating the mixture with a hydrogen chloride-containing gas at about 300°–700° C.

20 Claims, No Drawings

PREPARATION OF ISOMERIZATION CATALYST COMPOSITION

BACKGROUND OF THE INVENTION

This invention relates to the preparation of Group VIII metal-containing catalyst compositions, which are effective as catalysts for isomerizing saturated $C_4$-$C_8$ hydrocarbons.

Supported Group VIII metal- and chloride-containing compositions for alkane isomerization reactions are well known, and are described in the patent literature, e.g., in U.S. Pat. Nos. 5,004,859 and 4,149,993. However, there are ever present incentives for the development of new, effective methods of preparing them.

SUMMARY OF THE INVENTION

It is an object of this invention to provide a novel method for preparing supported, Group VIII metal- and chloride-containing catalyst compositions. It is a specific object of this invention to prepare a catalyst composition which comprises platinum, chloride and alumina. It is another specific object of this invention to prepare a catalyst composition which comprises palladium, chloride and alumina. It is still another specific objective to prepare a catalyst composition comprising nickel, chloride and alumina. Other objects and advantages will become apparent from the detailed description and the appended claims.

In accordance with this invention, a method of preparing a solid Group VIII metal- and chlorine-containing composition comprises:

(1) mixing dry aluminum chloride ($AlCl_3$) with a solid material which comprises (i) at least one Group VIII metal selected from the group consisting of platinum, palladium and nickel and (ii) alumina as the support;

(2) heating the mixture obtained in step (1) in a substantially inert gas atmosphere at a temperature of about 450°–700° C. for a time period of at least about 10 minutes; and (3) treating the material obtained in step (2) with a hydrogen chloride-containing gas at a temperature of about 300°–700° C. for a time period of at least about 10 minutes.

Preferably, the solid material comprising components (i) and (ii) which is used in step (1) has been prepared by a method comprising:

(a) impregnating alumina with at least one compound of a Group VIII metal selected from the group consisting of platinum, palladium and nickel;

(b) calcining the impregnated alumina obtained in step (a) at a temperature of about 300°–650° C. for a time period of at least about 10 minutes; and (c) treating the calcined material obtained in step (b) with a reducing gas (preferably a free-hydrogen-containing gas) at a temperature of about 200°–550° C. for a time period of at least about 10 minutes.

DETAILED DESCRIPTION OF THE INVENTION

Any suitable alumina material can be used in step (a) of the preparation method of this invention. Suitable aluminas include (but are not limited to) hydrated aluminas (such as beohmite, pseudoboehmite, bayerite), alpha-alumina, beta-alumina, gamma-alumina, delta-alumina, eta-alumina and theta-alumina, preferably gamma-alumina. The alumina material generally has a surface area (determined by the BET method of Brunauer, Emmett and Teller employing $N_2$) of about 100–400 $m^2/g$, a pore volume (measured by nitrogen intrusion porosimetry) of about 0.2–1.0 $cm^3/g$, and a particle size of about 8–200 mesh. The alumina particles can be spherical, cylindrical, trilobal, or can have any other suitable shape. The presently preferred alumina particles are cylindrical extrudates. It is within the scope of this invention to have small amounts of titanium (generally as $TiO_2$, at a level of about 0.05–1 weight-% Ti) present in the alumina material used in step (a).

Any suitable platinum compound (preferably water-soluble) can be used as the at least one Group VIII metal compound in step (a) of the preparation method of this invention. Suitable Pt compounds include (but are not limited to) platinum(II) chloride, platinum(IV) chloride, hexachloroplatinic(IV) acid, ammonium hexachloroplatinate(IV), tetrammineplatinum(II) chloride, tetrammineplatinum(II) carbonate, tetrammineplatinum(II) hydroxide, dichlorodiammineplatinum(II), tetrachlorodiammineplatinum(IV), platinum(II) nitrate, platinum(IV) nitrate, hexammineplatinum(II) nitrate, hexammineplatinum(IV) nitrate, diammineplatinum(IV) nitrite, diammineplatinum(II) oxalate, and many other complex (coordination) compounds of divalent and tetravalent platinum. Presently preferred is hexachloroplatinic acid, $H_2PtCl_6$.

Any suitable palladium compound (preferably water-soluble) can be used as the at least one Group VIII metal compound in step (a) of the preparation method of this invention. Suitable Pd compounds include (but are not limited to) palladium (II) chloride, palladium(II) nitrate, palladium(II) sulfate, palladium(IV) chloride, hexachloropalladic(IV) acid ($H_2PdCl_6$), ammonium hexachloropalladate(IV), tetramminepalladium(II) nitrate, tetramminepalladium(II) chloride, tetramminepalladium(IV) nitrate, tetrammine palladium(IV) chloride, and other coordination compounds of divalent and tetravalent palladium.

Any suitable nickel compound (preferably water-soluble) can be used as the at least one Group VIII metal compound in step (a) of the preparation method of this invention. Suitable Ni compounds include (but are not limited to) nickel(II) chloride, nickel(II) nitrate, nickel(II) sulfate, ammonium nickel(II) sulfate, nickel(II) acetate, nickel(II) oxalate, hexamminenickel(II) chloride, hexamminenickel(II) nitrate, hexamminenickel(II) sulfate, and other coordination compounds of divalent nickel. Presently preferred is nickel(II) nitrate, more preferably $Ni(NO_3)_2 \cdot 6H_2O$.

It is within the scope of this invention to have a dissolved titanium compound also present in step (a) of the preparation method of this invention, in particular when the alumina contains no Ti.. Any soluble (preferably water soluble) titanium compound can be used in step (a), either before or simultaneously with or after the impregnation with at least one compound of at least one Group VIII metal (more preferably platinum). Suitable Ti compounds which can be employed in this embodiment include (but are not limited to) titanium halides (such as $TiCl_4$), tetraalkyl titanates of the general formula $Ti(OR)_4$ wherein each R is an alkyl group (such as tetraethyl titanate, tetra-n-propyl titanate, tetraisopropyl titanate, tetrabutyl titanates), and water-soluble alkanolamine titanates (such as those described in U.S. Pat. Nos. 2,824,114; 2,935,522; 2,950,174; 3,028,297; 3,694,475; 3,892,791 and 4,621,148). These latter compounds are generally prepared by reacting one mole of a tetraalkyl titanate with 1–4 (preferably 2) moles of an alkanolamine selected from the group consisting of ethanolamine, diethanolamine, triethanolamine (preferred), monoisopropylamine, diisopropylamine and triisopropylamine. Each of the alkyl (R) groups (which may be the same as or different from one another) of the tetraalkyl titanate, $Ti(OR)_4$, generally contains 2–4 carbon atoms, and preferably is the isopropyl group. A particular alkanolamine titanate which can be used in step (a) of the method of this invention is prepared by the reaction of 1 mole of tetraisopropyl titanate, $Ti(OC_3H_7)_4$, with 2 moles of triethanolamine, also referred to as tri(2-hydroxyethyl)amine, thus forming primarily diisopropyl-bis(triethanolamine) titanate. A solution containing 80 weight-% of diisopropyl-bis(triethanolamine) titanate and 20 weight-% of isopropanol is commercially available from DuPont de Nemours and Co., Wilmington, Del., under the product designation of "TYZOR" TE TITANATE (wherein "TYZOR" is a registered trademark of DuPont).

The alumina material can be impregnated in step (a) with at least one dissolved Group VIII metal compound in any suitable manner, such as by incipient wetness impregnation, or by spraying with an impregnating solution containing at least one dissolved Group VIII metal compound. Generally, the total concentration of the at least one Group VIII metal compound (i.e., at least one Pt compound or at least one Pd compound or at least one Ni compound or mixtures of compounds of different Group VIII metals) in the impregnating solution generally is in the range of about 0.01–2 mol/l. Preferably, the solvent of the impregnating solution is an alcohol (such as ethanol) and/or water (the latter being presently preferred). If it is desired to also impregnate the alumina with at least one Ti compound (in particular, when the at least one Group VIII metal compound is at least one Pt compound), this can be done before or concurrently with or after the impregnation with the at least one Group VIII metal compound. The concentration of the Ti compound in the impregnating solution generally is about 0.01–2 mol/l. The solvent of this impregnating solution can be water and/or an alcohol (such as ethanol) or any other suitable liquid in which the particular Ti compound is soluble and stable. The weight ratio of the Group VIII metal-containing impregnating solution to alumina in step (a) is such as to attain a weight percentage of about 0.1–5 (preferably about 0.2–2) weight-% Group VIII metal (on an elemental basis) in the finished composition (i.e., the material obtained in the last step of the preparation method of this invention). If impregnation with at least one Ti compound is also carried out, the weight ratio of the Ti-containing impregnating solution to the alumina material generally is such as to attain a weight percentage of about 0.05–1.0 weight-% Ti (on an elemental basis) in the finished composition.

In step (b), the Group VIII metal impregnated alumina material is heated (calcined) at a temperature of about 300°–650° C. (preferably 450°–550° C.), generally for a time period of about 0.5–20 hours (preferably about 2–4 hours). This calcining step can be done in an inert atmosphere (e.g., $N_2$, He, Ne, Ar and the like) or in an $O_2$-containing atmosphere (e.g., air). Preferably, a drying step (generally at about 80°–150° C.) precedes heating step (b).

In step (c), the calcined material obtained in step (b) is treated with a reducing gas, generally a gas (preferably a gas stream) which generally comprises (preferably consists essentially of) free hydrogen ($H_2$), generally at a temperature of about 200°–550° C. (preferably about 350°–450° C.) for a time period of about 0.5–10 hours. Other, less preferred reducing gases include (but are not limited to) carbon monoxide, $C_1$-$C_6$ alkanes, and $C_2$-$C_6$ alkenes and $C_4$-$C_6$ alkadienes.

In step (1) of the preparation method of this invention, dry $AlCl_3$ is mixed with a Group VIII metal-containing alumina, preferably one having been obtained by the above-described method comprising steps (a)–(c). Generally, the weight ratio of $AlCl_3$ to the Group VIII metal-impregnated alumina is in the range of about 0.05:1 to about 1:1, preferably about 0.1:1 to about 0.3:1. $AlCl_3$ is generally applied in step (1) as a dry powder which is mixed with the Group VIII metal-impregnated alumina, preferably in a dry, inert gas environment.

In step (2), the mixture obtained in the previous step is heated to a temperature at about 450°–700° C. (preferably about 625°–675° C.), generally for a period of time of about 0.5–20 hours (preferably about 0.5–2 hours). This heating is carried out in an inert gas stream (e.g., $N_2$, He, Ar), preferably in an upflow mode. It is presently preferred to carry out preliminary heating steps (more preferably in upflow inert gas streams) before step (2): heating the mixture obtained in step (1) from room temperature (about 10°–40° C.) to a temperature of about 200°–250° C. within a time period of about 0.5–5 hours, heating the material at about 200°–250° C. for a time period of about 1–20 hours, and increasing the temperature from about 200°–250° C. to about 450°–700° C. (more preferably about 625°–675° C.) within a time period of about 0.5–3 hours. A particularly preferred mode of operation is described in Example IV.

Chlorination step (3) is carried out by heating with an HCl-containing gas. The HCl treatment step is carried out at a temperature of about 300°–700° C. (more preferably about 400°–650° C.) for a period of time of about 0.2–20 hours (preferably about 0.5–2 hours). Pure HCl gas can be used, but generally HCl is diluted with an inert gas (e.g., $N_2$, He, Ne, Ar), preferably such that the HCl-containing gas mixture contains about 10–30 weight-% HCl. The HCl-treated material generally is cooled to room temperature (about 10°–40° C.), preferably in an inert gas atmosphere. Preferably, step (3) is carried out in an upflow mode, which generally results in a more uniform finished catalyst.

The finished catalyst composition obtained in step (3) generally comprises about 0.1–5 (preferably about 0.2–2) weight-% of Group VIII metal (Pt and/or Pd and/or Ni) and about 2–7 (preferably about 4–5) weight-% Cl (chemically bound as chloride). The surface area, pore volume, shape and particle size of the finished catalyst composition are approximately the same as those of the alumina starting material (recited above).

The catalyst prepared by the method of this invention can be employed in the isomerization of saturated $C_4$-$C_8$ hydrocarbons (alkanes and/or cycloalkanes, preferably normal alkanes). Examples of suitable feed hydrocarbons include (but are not limited to) normal butane, normal pentane, normal hexane, normal heptane, normal octane, cyclohexane, methylcyclopentane, cycloheptane and methylcycloheptane (more preferably n-butane), generally in the presence of hydrogen. These so-called hydroisomerization processes are well known and have been described in the patent literature (e.g., in U.S. Pat. Nos. 4,149,993 and 5,004,859). Generally, hydrogen is mixed with the saturated feed hydrocarbon to form a feed mixture which is contacted with the isomerization catalyst of this invention contained in an isomerization zone. The concentration of the hydrogen in the feed mixture during this contacting step shall be such as to provide a hydrogen:hydrocarbon molar ratio of at least about 0.01:1, generally about 0.01:1 to about 5:1, preferably about 0.02:1 to about 2:1. The basic isomerization reaction conditions are well known and can be varied to achieve the desired conversion of the feed hydrocarbon to the desired isomer in a manner known in the art. Also, the recovery of the product isomer from the reaction mixture can be carried out by any suitable separation technique, such as fractional distillation. Isomerization of normal butane (n-butane) to isobutane is the presently preferred reaction carried out with the catalyst composition of this invention.

Generally, the saturated feed hydrocarbon and $H_2$ are contacted with the catalyst (generally present in a fixed bed) at a reaction temperature of at least about 200° F., preferably at a temperature of about 200°–500° F. In the preferred case of n-butane isomerization, the temperature is generally about 250°–400° F. Generally, the liquid hourly space velocity of the saturated hydrocarbon feed stream, i.e., cc of liquid feed hydrocarbon per cc of catalyst per hour, is about 0.1 to about 15. Generally, the reaction pressure is within the range of 200 psig to about 1500 psig in the isomerization zone. The gas hourly space velocity of the hydrogen feed stream is generally about 10–2,000 (preferably about 50–950) cc $H_2$ per cc catalyst per hour (so as to give the above-recited $H_2$: hydrocarbon ratio). In order to activate the catalyst and to retard its deactivation during the isomerization reaction, about 0.001 to about 1 weight percent chloride is frequently added to the alkane feed, generally in the form of at least one chloroalkane (described above), preferably carbon tetrachloride, chloroform, ethyl chloride or isopropyl chloride.

When the catalyst, after it has been in use in the hydroisomerization process, has lost its activity to the extent that the desired alkane conversion can no longer be attained at the desired reaction temperature, the catalyst can be reactivated by turning off the flow of the saturated feed hydrocarbon while maintaining the flow of the $H_2$ stream through the isomerization catalyst, generally at about the same gas hourly space velocity of $H_2$ as in the isomerization reaction. The temperature in this reactivation step is generally about the same as in the isomerization reaction, but may be readjusted upward or downward to maximize the reactivation effect. In the preferred reactivation mode, a reducing gas stream consisting essentially of hydrogen is passed through the partially deactivated isomerization catalyst bed at a temperature of about 80°–350° F. (preferably about 250°–330° F.) and a GHSV (gas hourly space velocity) of about 10–2,000 cc $H_2$ per cc catalyst per hour (more preferably about 50–950 cc/cc/hour), for a time period of about 2 hours to about 10 days (more preferably about 5 hours to about 7 days). Thereafter, the reactivated catalyst is redeployed in the alkane hydroisomerization of saturated $C_4$-$C_8$ hydrocarbons, as described above.

The following examples are provided to further illustrate this invention and are not to be considered as unduly limiting the scope of this invention.

EXAMPLE I

This example illustrates the preparation of several chlorinated Group VIII metal-containing alumina compositions (useful as catalysts for alkane and/or cycloalkane isomerization).

Catalyst A1 (Control was prepared as follows: About 130.0 g dry gamma-alumina (provided by Criterion Catalyst Company, Houston, Tex.) was impregnated (by incipient wetness at room temperature in an air atmosphere) with an aqueous platinum-containing solution containing 1.13 g $H_2PtCl_6$, 1.13 g HCl and 73.67 g $H_2O$. The Pt-impregnated material was air-dried (first under vacuum at room temperature, then at about 125° C.), heated for 2 hours in air at about 525° C., and then reduced by treating for 2 hours in flowing hydrogen gas at 425° C. 15.0 grams of the reduced material, which contained about 0.34 weight-% Pt, was then heated in an upflowing He/HCl gas stream (flow rate of He: 300 cc/minute; flow rate of HCl: 300 cc/minute) for 1 hour at 650° C. The HCl-treated material was cooled to room temperature and mixed with 2.00 g dry $AlCl_3$. The obtained mixture was then heated at 650° C. in a dry helium gas stream (flow rate: 50 cc/minute) for 2 hours, followed by cooling to room temperature in the dry He atmosphere.

Catalyst A2 (Invention) was prepared in accordance with the preparation method of this invention (which comprises HCl treatment after treatment with $AlCl_3$) as follows: 130.0 g dry alumina (from Criterion Catalyst Company) was impregnated (by incipient wetness at room temperature in an air atmosphere) with a solution containing 1.13 g $H_2PtCl_6$, 1.13 g HCl and 73.67 g $H_2O$. After about 2 hours of contact between alumina and the Pt-containing impregnating solution, the soaked material was dried for 96 hours in air at room temperature and then for 2 hours in air at 125° C., followed by calcining for 2 hours in air at 525° C., reducing for 2 hours in a $H_2$ gas stream at 425° C., and cooling to room temperature. 15 g of the reduced material, which contained 0.34 weight-% Pt, was mixed with 2.00 g dry $AlCl_3$. The mixture was then heated in an upflowing He gas stream to 650° C., heated in an upflowing He/HCl gas stream (flow rate of He: 40 cc/minute, flow rate of HCl: 300 cc/minute) for 2 hours at 650° C., cooled in this gas stream to 150° C., and finally cooled to room temperature.

Catalyst B1 (Control) was prepared essentially in accordance with the procedure for Catalyst A1, except that the temperature of the treatment with the He/HCl gas stream was 400° C. (instead of 650° C.).

Catalyst B2 (Invention) was prepared essentially in accordance with the procedure for Catalyst A2, except that the temperature of the treatment with the He/HCl gas stream was 400° C. (instead of 650° C.).

Catalyst C (an Intermediate) was prepared as follows: 32.1 g alumina (from Criterion Catalyst Company) with a mixed solution of 1.35 "TYZOR" TE TITANATE (provided by DuPont Chemicals, Wilmington, Del., containing about 80 weight-% diisopropylbis(triethanolamine) titanate, also referred to as isopropoxy(triethanolaminato) titanium and 20 weight-% isopropanol) in 15 g $H_2O$. The obtained mixture was dried and then calcined for 3 hours in air at 525° C. The calcined material was cooled to room temperature, impregnated (by the incipient wetness method) with a solution containing 0.30 g $H_2PtCl_6$, 0.30 g HCl and 15.50 g $H_2O$, dried, heated for 2 hours in air at 525° C., and heated for 2 hours in a hydrogen gas stream at 400° C. The cooled, reduced material (labeled Catalyst C) contained 0.36 weight-% Pt and 0.35 weight-% Ti.

Catalyst C1 (Control) was prepared as follows: 15.0 g Catalyst C was heated for 2 hours in an upflowing He/HCl gas stream (flow rate of He: 40 cc/minute, flow rate of HCl: 300 cc/minute) at 650° C. and then cooled to room temperature. The HCl-treated Catalyst C was mixed with 2.00 g dry $ACl_3$ and the mixture was heated in a He stream (flow rate: 40 cc/minute) at 650° C., followed by cooling.

Catalyst C2 (Invention) was prepared as follows: 15.0 g Catalyst C was mixed with 2.00 g dry $AlCl_3$ at room temperature. The mixture was heated in an upflowing He gas stream (flow rate: 40 cc/minute) to 650° C., heated for 2 hours at this temperature in this He gas stream, cooled in this He gas stream to 400° C., heated in an upflowing He/HCl gas stream (flow rate of He: 300 cc/minute; flow rate of HCl: 300 cc/minute), and cooled in this He/HCl stream.

Catalyst D (an Intermediate) was prepared as follows: 31.0 g alumina (from Criterion Catalyst Company) was impregnated (by incipient wetness) with an aqueous solution containing 2.55 g Ni(NO$_3$)$_2$·6H$_2$O and 14.45 g H$_2$O. The Ni-impregnated material was air-dried for 20 hours at room temperature, heated for 2 hours at 500° C. in air and then for 2 hours at 400° C. in hydrogen gas. Catalyst D contained 1.74 weight-% Ni.

Catalyst D1 (Control) was prepared as follows: 15.0 g Catalyst D was heated for 2 hours in an upflowing HCl gas (flow rate: 300 cc/minute) at 400° C. The HCl-treated material was then cooled and mixed with 2.0 g dry AlCl$_3$. The mixture was heated for about 2 hours at 650° C. in an upflowing helium gas stream (flow rate: 40 cc/minute) and was then allowed to cool in the He gas stream.

Catalyst D2 (Invention) was prepared as follows: 15.0 g Catalyst D was mixed with 2.00 g dry AlCl$_3$. The mixture was heated for 2 hours in an upflowing He gas stream (flow rate: 40 cc/minute) at 650° C., cooled in the He gas stream to 400° C., heated for about 1.5 hour in an upflowing He/HCl gas stream (flow rate of He: 300 cc/minute; flow rate of HCl: 300 cc/minute), and allowed to cool to 90° C. in a helium gas stream (flow rate: 300 cc/minute)

EXAMPLE II

This example illustrates the performance of the catalyst compositions described in Example I in the isomerization of n-butane.

20 cc of each catalyst was placed in a stainless steel reactor tube having an inner diameter of 1 inch and a length of 28 inches. The steel reactor tube was heated to about 138° C. A stream of hydrogen gas was passed through the catalyst bed at a rate of 1.34 cubic feet per hour. The reactor pressure was about 500 psig. Liquid n-butane was introduced at a rate of 78.2 cc/hour (liquid hourly space velocity: 3.9 cc/cc catalyst/hour), while the flow of the hydrogen gas stream was maintained at 1.34 ft$^3$/hour so as to provide a molar ratio of H$_2$ to n-butane of about 50:1. After the hydrogen/n-butane mixture had passed through the catalyst bed at the above conditions for about 10 minutes, carbon tetrachloride was injected into this feed mixture at a rate of 16 microliters per hour for a time period of up to 22–24 hours. Thereafter, the CCl$_4$ feed rate was reduced to 6 microliters per hour, and the test was continued. The isomerization product was analyzed by means of a gas chromatograph. Pertinent catalyst preparation parameters and isomerization test results (obtained at comparable reaction times) are summarized in Table I.

TABLE I

| Catalyst | Wt-% Promoter(s) in Catalyst | First Chlorination Agent | Temp. (°C.) | Second Chlorination Agent | Temp. (°C.) | n-Butane Isomerization Reaction Time (hr.) | % of Isobutane in Product |
| --- | --- | --- | --- | --- | --- | --- | --- |
| A1 (Control) | 0.34% Pt | HCl | 650 | AlCl$_3$ | 650 | 24 | 2.6 |
| A2 (Invention) | 0.34% Pt | AlCl$_3$ | 650 | HCl | 650 | 22 | 14.5 |
| B1 (Control) | 0.34% Pt | HCl | 400 | AlCl$_3$ | 650 | 22 | 2.7 |
| B2 (Invention) | 0.34% Pt | AlCl$_3$ | 650 | HCl | 400 | 22 | 16.0 |
| C1 (Control) | 0.36% Pt + 0.35% Ti | HCl | 650 | AlCl$_3$ | 650 | 22 | 2.5 |
| C2 (Invention) | 0.36% Pt + 0.35% Ti | AlCl$_3$ | 650 | HCl | 400 | 22 | 18.0 |
| D1 (Control) | 1.74% Ni | HCl | 400 | AlCl$_3$ | 650 | 22 | 2.7 |
| D2 (Invention) | 1.74% Ni | AlCl$_3$ | 650 | HCl | 400 | 22 | 17.8 |

Test data in Table I clearly show that the catalysts prepared by the method of this invention (comprising chlorination with aluminum chloride before chlorination with HCl) were significantly more active as n-butane isomerization catalysts than those prepared by a method comprising HCl treatment before chlorination with AlCl$_3$. Additional tests (carried out in autoclaves, not described herein in detail) indicate that Invention Catalysts A2, B2 and D2 were also quite effective as catalysts for the isomerization of n-hexane to isohexanes and of methylcyclopentane to cyclohexane at room temperature (Catalyst C2 was not tested).

EXAMPLE III

This example further illustrates the preparation method of this invention. The following catalyst compositions were prepared substantially in accordance with the preparation methods described for Catalysts A2 and C2 (see Example I) except that the employed alumina material was provided by United Catalysts, Inc. (UCI; Louisville, Ky.) under the product designation "CS-331-4". This material contains a small amount of Ti (as oxide). The thus-produced catalysts were tested in accordance with the procedure described in Example II. Pertinent preparation parameters and isomerization test results are summarized in Table II.

TABLE II

| Catalyst | Wt-% Promoter(s) in Catalyst | First Chlorination Agent | Temp. (°C.) | Second Chlorination Agent | Temp. (°C.) | n-Butane Isomerization Reaction Time (hr.) | % of Isobutane in Product |
| --- | --- | --- | --- | --- | --- | --- | --- |
| E (Invention) | 0.33% Pt | AlCl$_3$ | 650 | HCl | 650 | 25 | 12.1 |
| F (Invention) | 0.31% Pt + 0.44% Ti | AlCl$_3$ | 650 | HCl | 650 | 25 | 10.1 |

Test data in Table II essentially confirm the results presented in Table I. It is to be noted that the addition of Ti in Catalyst F had essentially no promoter effect (compare Catalyst F with Catalyst E). UCI's alumina contains a small amount of Ti (as TiO$_2$), and it is believed that additional impregnation with "TYZOR" TE TITANATE (see Example I) incorporated more than the optimal amount of Ti into the catalyst. Thus, in the case of the use of alumina starting materials which contain about 0.05–1.0 weight-% Ti, it is not preferred to carry out an impregnation with a titanium compound (in addition to impregnation with a Group VIII metal compound).

EXAMPLE IV

This example illustrates a modified method for preparing catalysts in accordance with the preparation method of this invention.

A Pt-promoted alumina which had been previously used in an isomerization reaction, provided by UCI under the product designation "UCI-331", was washed for 0.5 hour with water then with an aqueous ammonia solution (pH =9) for 1 hour and again with water, followed by drying, calcining in air at 550° C. for 6 hours and treatment with $H_2$ gas at 410° C. for 2 hours.

36.0 g of this reduced $Pt/Al_2O_3$ material was then mixed with 6.0 g dry $AlCl_3$. The mixture was placed in a quartz tube on top of a bottom layer of 36 grid Alundum® (an inert alumina having a surface area of less than 1 $m^2/g$). A top layer of Alundum® was placed on top of the mixture of $Pt/Al_2O_3$ and $AlCl_3$. The bottom Alundum® layer and the $Pt/Al_2O_3$—$AlCl_3$ layer were then heated to a temperature of 250° C. (at a rate of 1° C./minute) in an upflowing stream of helium gas (flow rate: 40 cc/minute), followed by heating at that temperature for about 16 hours in flowing He. Unreacted $AlCl_3$ sublimed and accumulated in the top Alundum® layer. Thereafter, the two bottom layers were cooled, and the top Alundum® layer (containing unreacted $AlCl_3$) was heated in the above-described He stream so as to remove the unreacted $AlCl_3$. Thereafter, the entire reactor tube was heated further in the above-described He stream to a temperature of 650° C. (at a rate of 10° C./minute), followed by heating in an upflowing He/HCl gas stream (flow rate of He: 40 cc/minute; flow rate of HCl: 300 cc/minute) at 650° C. for 2 hours and cooling in an upflowing He/HCl gas stream (flow rate of He: 300 cc/minute; flow rate of HCl: 300 cc/minute) from 650° C. to 150° C. Finally, the chlorided catalyst was cooled to room temperature in a He gas stream. The thus-prepared catalyst was tested in preliminary autoclave tests (not described in detail herein) for n-hexane and for methylcyclopentane isomerization activity (at room temperature). Both tests revealed high feed conversions of each feed hydrocarbon (to isohexanes and cyclohexane, respectively).

Reasonable variations, modifications and adaptations for various conditions and reactants can be made within the scope of the disclosure and the appended claims without departing from the scope of this invention.

That which is claimed:

1. A method of preparing a solid Group VIII metal- and chlorine-containing composition which comprises:
    (1) mixing dry aluminum chloride with a solid material which comprises (i) at least one Group VIII metal selected from the group consisting of platinum, palladium and nickel and (ii) alumina as the support;
    (2) heating the mixture obtained in step (1) in a substantially inert gas atmosphere at a temperature of about 450°–700° C. for a time period of at least about 10 minutes; and
    (3) treating the material obtained in step (2) with a hydrogen chloride-containing gas at a temperature of about 300°–700° C. for a time period of at least about 10 minutes;

wherein said solid material used in step (1) is a reduced material having been prepared by a method consisting essentially of the steps of:
    (a) impregnating an alumina material with at least one compound of a Group VIII metal selected from the group consisting of platinum, palladium and nickel;
    (b) drying and then calcining the impregnated alumina material obtained in step (a) at a temperature of about 300°–650° C. for a time period of at least about 10 minutes; and
    (c) heating the calcined material obtained in step (b) with a reducing gas comprising free hydrogen at a temperature of about 200°–550° C. for a time period of at least about 10 minutes so as to obtain a reduced material.

2. A method in accordance with claim 1, wherein the weight ratio of $AlCl_3$ to said solid material in step (1) is about 0.05:1 to about 1:1, the time period of step (2) is about 0.5–20 hours, and the time period of step (3) is about 0.5–20 hours.

3. A method in accordance with claim 2, wherein the temperature in step (2) is about 625°–675° C. and the temperature in step (3) is about 400°–650° C.

4. A method in accordance with claim 2, wherein said at least one Group VIII metal is platinum.

5. A method in accordance with claim 2, wherein said at least one Group VIII metal is palladium.

6. A method in accordance with claim 2, wherein said at least one Group VIII metal is nickel.

7. A method in accordance with claim 2, wherein step (2) is carried out in an inert gas stream in an upflow mode, and step (3) is carried out with a gas stream comprising HCl and an inert gas in an upflow mode.

8. A method in accordance with claim 7, wherein the following heating steps are carried out in inert gas streams in an upflow mode before step (2): increasing the temperature of the material obtained in step (1) from about 10°–40° C. to about 200°–250° C., heating said material obtained in step (1) at a temperature of about 220°–250° C. for a time period of about 1–20 hours, and increasing the temperature of said material obtained in step (1) from about 200°–250° C. to about 450°–700° C.

9. A method in accordance with claim 1, wherein step (b) is carried out for a time period of about 0.5–20 hours, and step (c) is carried out for a time period of about 0.5–20 hours.

10. A method in accordance with claim 1, wherein step (a) is carried out with at least one dissolved platinum compound.

11. A method in accordance with claim 10, wherein said alumina material is also impregnated with at least one dissolved titanium compound.

12. A method in accordance with claim 1 wherein step (a) is carried out with at least one dissolved palladium compound.

13. A method in accordance with claim 1, wherein step (a) is carried out with at least one dissolved nickel compound.

14. A method in accordance with claim 1, wherein the material obtained in step (3) comprises about 0.1–5 weight-% of said at least one Group VIII metal and about 2–7 weight-% chlorine.

15. A method in accordance with claim 14, wherein said at least one Group VIII metal is platinum.

16. A method in accordance with claim 14, wherein said at least one Group VIII metal is palladium.

17. A method in accordance with claim 14, wherein said at least one Group VIII metal is nickel.

18. A method in accordance with claim 1, wherein said alumina material used in step (a) contains about 0.05–1 weight-% Ti.

19. A process in accordance with claim 1, wherein said reducing gas used in step (c) is a gas stream consisting essentially of free hydrogen.

20. A method of preparing a solid Group VIII metal- and chlorine-containing composition which comprises:

(1) mixing dry aluminum chloride with a solid material which comprises (i) at least one Group VIII metal selected from the group consisting of platinum, palladium and nickel and (ii) alumina as the support;

(2) heating the mixture obtained in step (1) in a substantially inert gas atmosphere at a temperature of about 450°–700° C. for a time period of at least about 10 minutes; and (3) treating the material obtained in step (2) with a gas stream consisting essentially of hydrogen chloride or, alternatively, consisting essentially of a mixture of hydrogen chloride and an inert gas at a temperature of about 300°–700° C. for a time period of at least about 10 minutes;

wherein said solid material used in step (1) is a reduced material having been prepared by a method consisting essentially of the steps of:

(a) impregnating an alumina material with at least one compound of a Group VIII metal selected from the group consisting of platinum, palladium and nickel;

(b) drying and then calcining the impregnated alumina material obtained in step (a) at a temperature of about 300°–650° C. for a time period of at least about 10 minutes; and (c) heating the calcined material obtained in step (b) with a reducing gas comprising free hydrogen at a temperature of about 200°–550° C. for a time period of at least about 10 minutes so as to obtain a reduced material.

* * * * *